US006187951B1

(12) United States Patent
Baniel et al.

(10) Patent No.: US 6,187,951 B1
(45) Date of Patent: *Feb. 13, 2001

(54) LACTIC ACID PRODUCTION, SEPARATION AND/OR RECOVERY PROCESS

(75) Inventors: Avraham M. Baniel; Aharon M. Eyal, both of Jerusalem; Joseph Mizrahi, Haifa; Betty Hazan, Jerusalem, all of (IL); Rod R. Fisher, Eden Prairie, MN (US)

(73) Assignee: Cargill, Incorporated, Minneapolis, MN (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

This patent is subject to a terminal disclaimer.

(21) Appl. No.: 08/556,384

(22) Filed: Nov. 13, 1995

Related U.S. Application Data

(63) Continuation-in-part of application No. 08/207,773, filed on Mar. 8, 1994, now Pat. No. 5,510,526, which is a continuation-in-part of application No. 08/084,810, filed on Jun. 29, 1993, now abandoned.

(51) Int. Cl.[7] .................................................. C07C 51/42
(52) U.S. Cl. ............................................ 562/580; 562/589
(58) Field of Search ..................................... 562/580, 589

(56) References Cited

U.S. PATENT DOCUMENTS

| 1,906,068 | 4/1933 | Jenemann . |
| 2,223,797 | 12/1940 | Tindall . |
| 2,539,472 | 1/1951 | Ratchford et al. .................... 260/535 |
| 4,275,234 | 6/1981 | Baniel et al. ......................... 562/584 |
| 4,282,323 | 8/1981 | Yates .................................... 435/140 |
| 4,405,717 | 9/1983 | Urbas . |
| 4,444,881 | 4/1984 | Urbas ................................... 435/139 |
| 4,698,303 | 10/1987 | Bailey et al. ......................... 435/139 |
| 5,071,754 | 12/1991 | Walkup et al. . |
| 5,132,456 | 7/1992 | King et al. ........................... 562/593 |
| 5,252,473 | 10/1993 | Walkup et al. ...................... 435/135 |
| 5,349,084 | 9/1994 | Shishikura et al. .................. 562/580 |
| 5,510,526 | 4/1996 | Baniel et al. ........................ 562/580 |

FOREIGN PATENT DOCUMENTS

| 517242 | 5/1992 | (EP) . |
| 0 517 571 | 12/1992 | (EP) . |
| 216221B1 | 7/1994 | (EP) ................................ C12P/1/00 |
| 33552 | 7/1969 | (IL) . |
| 7-258 154 | 10/1995 | (JP) . |
| 04192 | 1/1993 | (WO) . |
| WO 95/24496 | 9/1995 | (WO) . |
| WO 97 30964 | 8/1997 | (WO) . |

OTHER PUBLICATIONS

Proceedings of the International Solvent Extraction Conference, vol. 3, issued 1974, R. Blumberg et al., "Interesting Aspects in the Development of a Novel Solvent Extraction Process for Producing Sodium Bicarbonate", pp. 2789–2802.

D. R. Johnson, "Lactic Acid Purification Processes", Moffat Research, Arga, IL Nov. 1970.

R. Blumberg et al., "A Process for the Manufacture of Alkali Metal Carbonates", 1972.

(List continued on next page.)

Primary Examiner—Gary Geist
Assistant Examiner—Sreeni Padmanabhan
(74) Attorney, Agent, or Firm—Merchant & Gould P.c.

(57) ABSTRACT

A process for the production and isolation of lactic acid is provided. A lactate feed solution, preferably obtained from a fermentation broth is combined with and extracted by a water-immiscible base in the presence of an acidifying agent. Lactic acid is recovered from the resulting organic phase. Recovered carbonate or bicarbonate from the aqueous phase can be recycled to the fermentor and regenerated extractant can be recycled for use in the extraction.

23 Claims, 1 Drawing Sheet

OTHER PUBLICATIONS

N.L. Ricker et al., "Solvent Extraction with Amines for Recovery of Acetic Acid from Dilute Aqueous Industrial Streams", J. Separ. Proc. Technol. 1(2) 23–30 (1980).

R. Bar and J.L. Geiner, Biotechnology Progress 3, 109 (1987).

Blumberg et al., "Interesting Aspects in the Development of a Novel Solvent Extraction Process for Producing Sodium Bicarbonate", Proc. Int. Solvent Extraction Conf. 1974, v.3.

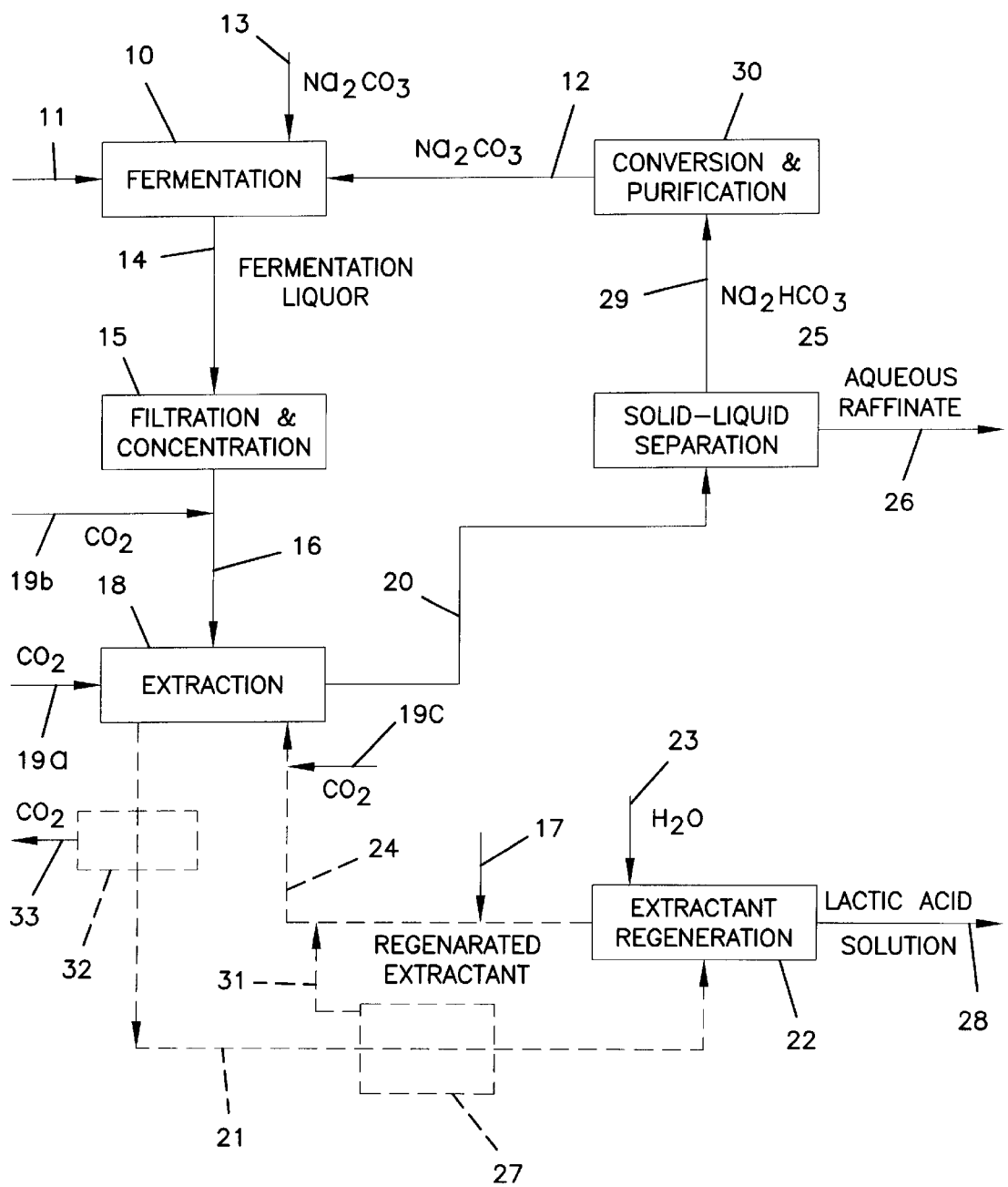

LACTIC ACID PRODUCTION, SEPARATION AND/OR RECOVERY PROCESS

CROSS REFERENCE TO RELATED APPLICATIONS

The present application is a continuation-in-part of application Ser. No. 08/207,773 filed Mar. 8, 1994, now U.S. Pat. No. 5,510,526. Application Ser. No. 08/207,773 was a continuation-in-part of application Ser. No. 08/084,810 filed Jun. 29, 1993, now abandoned. The complete disclosures of Ser. No. 08/084,810 and Ser. No. 08/207,773 are incorporated herein by reference.

BACKGROUND OF THE INVENTION

1. Field of the Invention

The present invention relates generally to the production, separation and/or recovery of lactic acid and more particularly to the production, separation and recovery of lactic acid via a fermentation process and the separation and/or recovery of lactic acid from a lactate feed solution such as is obtained from a fermentation broth or other sources.

2. Description of the Prior Art

Lactic acid has long been used as a food additive and in various chemical and pharmaceutical applications. More recently, lactic acid has been used in the making of biodegradable polymers both as a replacement for present plastic materials as well as various new uses where biodegradability is needed or desired. Accordingly, there is an ever increasing demand for lactic acid. The present invention aims at meeting this demand by providing an efficient and environmentally friendly process for producing lactic acid, that can, if desired, be employed to avoid the consumption of bases and acids; and, that can be used, if desired, to substantially reduce, if not eliminate, the formation of waste or byproduct salts.

Production of lactic acid is commonly carried out by fermentation of a strain of the bacterial genus Lactobacillus and more particularly by the species *Lactobacillus delbrueckii* or *Lactobacillus acidophilus* as examples. In general, the production of lactic acid by fermentation in a fermentation broth is well known. The fermentation substrate consists of carbohydrates together with suitable mineral and proteinaceous nutrients. Because the lactic acid producing microorganisms are inhibited in a strongly acidic environment, the pH of the fermentation broth must be kept above 4.5, and preferably within the range of about 5.0 to 7.0, more preferably within the range of about 5.5 to 6.5, and most preferably within the range of about 6.0 to 6.5. To maintain this pH level, suitable water-soluble basic substances or agents that are non-toxic to the acid producing microorganism, such as alkali metal hydroxides, carbonates or bicarbonates or alkaline earth metal hydroxides or carbonates, are commonly added to the fermentation broth to neutralize the acid being produced. This results in the formation of a lactate solution rather than the desired lactic acid product. Such lactate solution contains the lactate anion and the corresponding cation of the substance used to neutralize the fermentation broth.

Various methods have been proposed for the recovery of lactic acid from a fermentation broth. Where the fermentation is carried out in the presence of calcium carbonate, it is possible to recover the lactic acid by acidification with sulfuric acid. This results in the precipitation of calcium sulfate, while free lactic acid remains in the mother liquor. If desired, the mother liquor may be concentrated to up to about 90% by weight lactic acid. Subsequently, lactic acid may be extracted from the mother liquor with a suitable organic extractant, to yield an extract which is later back-extracted with water, or the acid may be adsorbed on a suitable adsorbent and later desorbed. The resulting aqueous lactic acid solution may then be concentrated. This method has the disadvantage, however, that it irreversibly consumes calcium carbonate and sulfuric acid and leaves, as waste, large quantities of calcium sulfate, which can give rise to disposal problems.

U.S. Pat. No. 5,132,456 (King et al.) describes a process for recovering carboxylic acid from a carboxylic acid-containing aqueous feed stream having a pH close to or above the $pK_a$ level of the acid. In accordance with that process the recovery involves what may be described as a cascade type acid withdrawal operation in which the basicity of the extractant is increased stepwise. In a first stage of the process, the feed stream is contacted with an adsorbent such as a strongly basic extractant or a solid anion exchanger. In a second stage the acid-loaded adsorbent is contacted with an aqueous solution of ammonia or a low molecular weight trialkyl amine having a stronger affinity to the carboxylic acid that is being recovered than the adsorber used in the first stage. In this way the aqueous solution of a water-soluble carboxylic acid ammonium salt is formed. This is then subjected to heat treatment, whereby the salt is decomposed to yield back the trialkyl amine or ammonia and free carboxylic acid. Applying this process to lactic acid involves the formation of salts of lactic acid with strong bases having a $pK_a$ value of about 9–11; i.e. the conjugate acid of the base has a $pK_a$ of 9–11. Thus, the decomposition of these salts into free lactic acid is energy intensive. Examples 12–14 of the '456 patent mention the use of Alamine 336 (tricaprylylamine) for the extraction of, among others, lactic acid from an aqueous solution, but no yields are mentioned. Upon the extraction of even small quantities of lactic acid from a fermentation broth the pH of the broth rises rapidly to above 7. As shown in FIGS. 3 and 4 of the '456 patent, the uptake of carboxylic acids from aqueous solutions drops rapidly with an increase of the pH. It is, therefore, inherent in these examples that the lactic acid uptake, if any, is negligible. It is further noted that upon heat treatment and concentration of an ammonium lactate, crystalline lactic acid does not precipitate and instead the viscosity of the solutions increases steadily as a result of self-association of the acid. It is thus evident that the process of U.S. Pat. No. 5,132,456 is unsuitable for the recovery of lactic acid from a fermentation broth.

U.S. Pat. Nos. 4,444,881 and 4,405,717 (Urbas) describe a process for the recovery of an organic acid from a diluted aqueous solution of its calcium salt by adding a water-soluble trialkyl amine carbonate to the solution to form on the one hand a water soluble trialkyl ammonium salt of the acid, which salt remains in solution, and on the other hand calcium carbonate which precipitates. After removal of the calcium carbonate the remaining mother liquor is heated for the separate recovery of the amine and the product acid. The decomposition of the trialkylammonium salts of this reference into free acids is energy intensive.

U.S. Pat. No. 4,282,323 (Yates) describes a process for obtaining lower carboxylic acids from a salt solution of such carboxylic acid as obtained from fermentation. The process appears to be applicable to a restricted number of lower aliphatic and aromatic monocarboxylic acids and is specifically described only in relation to acetic acid. In accordance with that process, the aqueous solution of a carboxylic acid salt is concentrated in the presence of a liquid polar organic solvent serving as extractant, with pressurized carbon dioxide, to convert at least part of the salt to the corresponding free acid which is taken up by the organic phase, from which it is subsequently recovered. It is inherent in the use of a polar organic extractant that the bulk of the carboxylic acid remains in the neutral to basic aqueous phase, and indeed the recovery rates reported in U.S. Pat. No. 4,282,323 are low, ranging between 4.8% and 18% of the acid initially present.

U.S. Pat. No. 4,275,234 (Baniel et al) is directed to a method of recovering various acids in their free form from aqueous solutions. Thus, the process of Baniel is not applicable to a lactate solution of the type commonly obtained from a fermentation process or from other sources. The essence of the Baniel et al. U.S. Pat. No. 4,275,234 is the discovery that efficient back-extraction can be achieved by performing the back-extraction at a temperature higher than that of the primary extraction.

R. Bar and J. L. Geiner, *Biotechnology Progress*, 3, 109 (1987) studied the feasibility of extracting lactic acid from aqueous solution by means of a long-chain trialkyl amine of low basicity, such as tridodecylamine, using various tridodecylamine solutions in n-dodecanol.

REVIEW OF THE DISCLOSURE OF U.S. Ser. No. 08/207,773

In accordance with the disclosure of U.S. Ser. No. 08/207,773, it was reported that it is possible to separate and recover lactic acid from a lactate solution at a pH in the range of 4 to 14 in a nearly quantitative fashion, with a desirable process. More specifically, the preferred lactic acid separation and recovery process reported includes an extraction hereinafter (sometimes referred to as the primary or forward extraction) in the presence of a water-immiscible, long-chain trialkyl amine and carbon dioxide. The lactate solution could be obtained from a fermentation broth or from hydrolyzed polylactide via polylactide recycling or recovery, among possible others.

In the parent disclosure, the invention is described as providing a process for the separation and/or recovery of lactic acid from a lactate solution formed by fermentation in the presence of a basic substance such as one selected from the group of alkali metal, alkaline earth metal or ammonium hydroxides, carbonates or bicarbonates. The process steps comprise obtaining a lactate feed solution from a fermentation broth or another source and combining such feed solution with an extractant. The particular preferred extractants disclosed are trialkyl amines, with the extraction being in the presence of carbon dioxide and with the trialkyl amine being water-immiscible and having a total of at least 18 carbon atoms. The term "combining" is explained in the parent as meaning a mixing or contacting of the lactate solution (aqueous phase) and the amine (organic phase) so that extraction can occur. It was recited that preferably the lactate feed solution is formed by filtering a fermentation broth to remove biomass and other solids and that the combining of the lactate solution and extractants preferably occurs in the presence of carbon dioxide at a partial pressure of at least about 50 psig.

The above extraction in accordance with the parent disclosure results in the formation of a lactic acid rich organic phase and an aqueous or aqueous-slurry phase. Each of these two phases, in accordance with preferred further aspects of the parent disclosure, is further processed: the processing being recovery of lactic acid from the organic phase and recovery of carbonate or bicarbonate from the aqueous phase. As explained in the parent, preferably the recovered carbonate or bicarbonate is recycled to the fermentor. The organic phase from which the lactic acid been recovered can be recycled for use in the primary extraction. If applied in the preferred manners described, this would result in a process in which the consumption of acids and bases is avoided and in which the generation of waste salts and other by-products is substantially reduced, if not eliminated.

In a preferred process of the parent disclosure, a countercurrent liquid—liquid extractor or extraction unit is used. During steady state operation, the lactate feed solution and extractant are loaded into the extractor and operated in the presence of pressurized carbon dioxide. The optimum operational pressure was described as not being critical, provided sufficient carbon dioxide is present for the primary extraction to occur. It was stated, however, that preferably the partial pressure of carbon dioxide is maintained at 50 psig or greater. It was described that upon leaving the extractor, the organic phase may be subjected to decompression. This would result in a release of the pressurized carbon dioxide which could, if desired, be recovered for reuse in the process.

The long-chain trialkyl amines described in the parent as useful and preferred are those in which the amines and the amine lactate salts are immiscible with water and have a total of at least 18 carbon atoms, and preferably have from 24 to 42 carbon atoms. Typical examples of such amines provided in the parent are trihexylamine, trioctylamine, triisooctylamine, tricaprylylamine and tridodecylamine. The parent disclosure states that the term "amine salt" or "amine lactate salt" refers to the species formed when lactic acid or lactate is extracted into the amine extractant phase, although the exact nature of this species is not known.

In the parent, the extraction process is described as being performed batchwise or continuously, but that dramatically improved separation and ultimate recovery can be achieved with a continuous process and in particular a countercurrent extraction process.

In the parent it is stated that solvents of the trialkyl amines may also be used, if desired, as part of the extractant. It is believed that these may be used for the purpose of diluting certain relatively viscous trialkyl amines, enhancing the extraction, and/or stabilizing and maintaining the organic phase in a single phase substantially immiscible with water. Any compatible organic solvent capable of dissolving the amine and the amine lactate salt would be suitable, provided it is also inert to chemical reaction both with the long-chain trialkyl amines utilized and to the amine lactate salt and lactic acid. In the parent, it was stated that the term "compatible" means miscible with, soluble in and chemically inert. The usefulness of solvents for these purposes is well known in the art. Specific examples, however, were described in the parent as liquid hydrocarbons such as kerosene or mineral oils, alkanols such as isopropanol, n-butanol and n-octanol and various ketones such as methyl-isobutyl ketone (MiBK) and nonanone, among others. In the parent it was stated that two or more different solvents may be used, for example a hydrocarbon and an alkanol.

According to the parent, the organic phase resulting from the primary or forward extraction is subjected to a separation process such as further extraction, vaporization or the like to recover the lactic acid. Also, it was stated that preferably the organic phase is subjected to back-extraction with water to recover the lactic acid in an aqueous phase. Where the initial extracting medium also contains an alkanol or ketone as a solvent, it was stated that the back-extraction may be preceded by removal of the solvent through azeotropic steam distillation or other techniques. It was also stated that the portion of the organic phase remaining after separation of the lactic acid and, where applicable, the separately recovered alkanol or ketone, can be recycled for use in the primary extraction. The aqueous lactic acid solution resulting from the back-extraction can be removed as product and can be concentrated, if desired.

In a preferred embodiment of the process described in the parent, carbonate or bicarbonate is present in the aqueous phase either in solution or as a solid suspension, predominantly in the form of an alkali metal, alkaline earth metal or ammonium carbonate or bicarbonate, depending on the cation present in the lactate solution. This aqueous phase is preferably a suspension of sodium bicarbonate crystals and is subjected to solid-liquid separation followed by conversion of the bicarbonate into sodium carbonate by heat treatment or other techniques known in the art. Carbon dioxide liberated during this conversion may be trapped and recycled for use in the primary extraction. The solid-liquid separation also yields an aqueous raffinate, substantially depleted of lactate, which is withdrawn and may be used as a constituent of animal feed.

SUMMARY

In this section, a general discussion of the principles presented in the parent disclosure Ser. No. 08/207,773 and its parent Ser. No. 08/084,810, is provided. This section includes some additional comment on those principles, beyond the specific language of the '773 and '810 applications.

In the Background section of the parent disclosure, a technique for lactic acid recovery involving acidification of a lactate solution including calcium lactate, by sulfuric acid, was described. In general, it was stated that after the fermentation broth was acidified with sulfuric acid, using this prior art technique, and the mother liquor is concentrated, the lactic acid is extracted with an organic extractant. It was generally shown that next the organic phase (water-immiscible phase) can be back-extracted with water (or the acid is adsorbed on a suitable absorbent) for isolation and recovery of the lactic acid. This method is a general method involving the acidification of the broth with strong acids. A strong acid can substantially lower the pH of the lactate solution, causing formation of undissociated lactic acid (i.e. no lactate but essentially only lactic acid) and a salt of the strong acid. In the technique, an extractant is then used to extract the undissociated acid. A principal problem with this approach is the generation of large amounts of the salt of the strong acid used in the acidification process. In addition, the salt of the strong acid is typically too weak a base to be useful as a base in the fermentation broth to provide lactate salt.

Also in the Background of the parent, the Yates '323 reference was discussed. It is noted that one of the carboxylic acids isolated during that process, is acetic acid. Acetic acid is a relatively weak organic acid. If a stronger organic acid were used in the process, it would typically be even more dissociated at a given or operating pH for the extraction, than was the acetic acid, unless a very basic operating pH were involved, i.e. one that ensured essentially all of the acid were dissociated. If the Yates' process (including extraction with a liquid polar organic solvent as the extractant) were used, one would expect even lower recovery of a stronger organic acid than Yates achieved for acetic acid, under the conditions of the process, since the process concerns recovery of the acid, not the anion or base form. The recovery rates reported in Yates '323 for acetic acid (4.8%–18%) were already relatively low. Thus, the Yates' approach would not be expected to be very fruitful, if an acid substantially stronger than acetic acid, for example lactic acid, were involved.

The techniques developed and reported in the parent disclosures (i.e. Ser. Nos. 08/207,773 and 08/084,810) concern and take advantage of the fact that lactic acid is moderate acid, not an extremely strong one and not an extremely weak one. For purposes of the description, generally a "strong acid" will be considered to be any acid with a $pK_a$ of 1.0 or less. A "moderate acid" would be one having a $pK_a$ greater than 1.0 and no greater than about 4.0. "Weak acids" would be those with a $pK_a$ greater than about 4.0. For purposes of classifying an acid according to this description, the $pK_a$ should generally be rounded to the nearest 0.1. In general, lactic acid, with a $pK_a$ of about 3.9, then, will be considered a moderate acid for purposes of this discussion. The $pK_a$ values in this paragraph refer to values at 25° C.; i.e. room temperature.

In the parent disclosures, reference was made to conducting extractions with immiscible amines such as long chain trialkyl amines. These are typically moderate bases. In general a "weak" base will be considered herein to be a base with a pH of half neutralization of less than 2.5; a moderate base will be considered to be a base with a pH of half neutralization of between 2.5 and 7.0; and, a strong base will be considered to be a base with a pH of half neutralization of greater than 7.0. The term "pH of half neutralization" is a measure of apparent basicity of a water-immiscible base, as defined in Grinstead, R. R. et al., *J. Phys. Chem.*, Vol. 72 #5, p. 1630 (1968), incorporated herein by reference.

In general, the invention concerns a process for recovery of lactic acid. The process includes the steps of forming a multi-phase system including at least a first aqueous phase and a second organic or water-immiscible phase. The first aqueous phase is provided in a form having a pH of 4 to 14 and including lactate salt in solution. The organic or water-immiscible phase preferably includes an extractant capable of forming a water-immiscible lactate salt, with a lactate-containing component.

The process includes a step of extracting a first aqueous phase with a water-immiscible phase by forming a water-immiscible lactate salt with the extractant. The step of forming the lactate salt generally includes a step of acidifying at least one of the first aqueous phase and the water-immiscible phase without providing the first aqueous phase with a pH below 4. The process further includes a step of separating the resulting water-immiscible phase from a resulting aqueous phase, after the step of extracting; and, obtaining or generating lactic acid from the lactate salt of the extractant found in the water-immiscible phase. This later step is typically conducted through a form of back-extracting. The step of acidifying is preferably conducted by adding an acid to either or both of the first aqueous phase and the second water-immiscible phase. It may be conducted either before these two phases are brought together, or after.

Herein reference will, in some instances, be made to "lactate-containing component" in the aqueous phase. This term is intended to refer to both the anion form, lactate anion; and, the acid form, lactic acid, together. Preferred processes result in extraction of at least 90% of the lactate-containing component in the first aqueous phase, and generally and preferably are conducted until at least 95% of this material is extracted into the water-immiscible phase (as lactic acid). Indeed, preferably the process is conducted such that ultimately such amounts (i.e. at least 90%, and typically 95% or greater) are found in the final yield after the step of lactic acid recovery from the water-immiscible phase.

In general, the lactic acid separation and recovery process of the invention concerns a step of extracting the lactate-containing component with a water-immiscible weak or moderate base. However, it is preferred that the lactate-containing component removed be removed after the acidifying by addition of a moderate to weak acid. The particular preferred acid disclosed in the parent, is gaseous $CO_2$, a weak acid which will generate carbonic acid in the solution. The carbonic acid, being a weak acid, will partly dissociate in the solution. Preferably the $CO_2$ is added to the water-immiscible phase, before the multi-phase system is formed.

The use of the weak or moderate base for conduct of the extraction is important, since it facilitates later recovery of the lactic acid from the organic phase or layer. In particular, especially if a back-extraction with an aqueous phase or layer is used for final isolation of the lactic acid, the weak or moderate base will not hold the lactic acid sufficiently strongly to resist the partitioning of the lactic acid back into the aqueous phase. Preferably the back-extraction is not conducted with a weak base alone. Preferably it is conducted with a moderate base, or a mixture of weak base and moderate base.

The use of a relatively weak acid to acidify, prior to extraction or during extraction, is also important. The relatively weak acid will form a salt in the aqueous phase which is a relatively strong base that can be used directly, or after mild conversion (for example from a bicarbonate to a carbonate), as a base in the fermentation broth. The use of a moderate acid is less preferable because in general the salt formed will be too weak a base to be readily useful as a base in the fermentation broth.

In general, the weak or moderate base, used for the extraction, will be considered immiscible if, under the extraction conditions, it is sufficiently insoluble in the aqueous phase or layer such that its presence will be no greater than about 1000 ppm, and preferred ones will have a presence of no greater than about 200 ppm. Typically, bases will be chosen that have a solubility of 100 ppm or less. The weak or moderate base could be presented in the form of a solid, and thus be completely immiscible in water.

Also, preferably the weak or moderate base is also immiscible in the water used in the later back extraction, if one is conducted. A base will be considered immiscible in the aqueous phase of the back extraction if the above-stated ppm limits for water-immiscibility during the first extraction are not exceeded.

From the above it will be apparent that the process steps of preferred lactic acid recovery processes, described in the parent applications, concern the following steps:

(1) Obtaining a lactate feed solution from a fermentation broth or other source;

(2) Modifying the lactate feed solution, preferably with a source of moderate or weak acid while maintaining a pH of at least 4, and preferably within the range of 4–14; and (3) Extracting the lactic acid with a water-immiscible weak or moderate base, or mixture.

In the preferred applications described, the water-immiscible weak or moderate base is a water-immiscible amine, typically an alkyl amine and preferably a water-immiscible tertiary amine. Preferably alkyl amines and most preferably water-immiscible trialkyl amines are used. As explained in the parent, the preferred water-immiscible amine will be a trialkyl amine containing at least a total of 18 carbon atoms.

In an alternate statement, typically when the extraction occurs, the aqueous phase is provided such that the lactate-containing component or species present, at any given time throughout the extraction, is at least 50% (molar equivalent) in the form of lactate, rather than the lactic acid. In general this is accomplished by appropriate control of the pH, and selection of the desirable acid for acidification of the system.

The preferred processes are conducted on lactate feed solutions that contain lactate values in a concentration of at least 3 mol. When the processes concern recovery from a fermentation broth, generally the fermentation process is conducted such that the feed solution contains at least 5%, and typically 10 to 30%, by weight, lactate. The broth may be concentrated, before extraction.

As also will be apparent from the parent disclosures, preferably the moderate or weak acid, used to acidify, is an acid which is either readily separated from the water-immiscible weak or moderate base, or which does not combine to any substantial extent with the water-immiscible weak or moderate base under the conditions of extraction. Carbon dioxide is an almost ideal acid for use in generation of the lactic acid, since its presence can so readily be controlled through control of its partial pressure, it can easily be removed from the solutions, it is relatively inexpensive, and it is such a weak acid that the salt which is generated is also very suitable for effective neutralization of fermentation broth. It is foreseen that in some instances the moderate or weak acid may comprise a salt of an acid having more than one proton; for example monosodium phosphate, provided the $pK_a$ for the remaining proton(s) is within the appropriate ranges.

In typical preferred applications, the acid which is used to acidify the multi-phase system is preferably a weaker acid (i.e. has a higher $pK_a$) than lactic acid. A reason for this preference is that the corresponding salt of the added acid, which will form in the aqueous phase, will be a useful base in the fermentation broth. Also, when used with the preferred extractants, such as the water-immiscible amines, an advantage results because of the extractant's preference for the stronger acid, i.e. lactic acid.

As indicated in the experiments, processes according to the invention are characterized by relatively high recoveries of the lactate values in the lactate containing feed solution (for example, the fermentation broth). Recoveries greater than 90% are readily achieved, and typically the recovery is at about 95% or greater.

With respect to the weak or moderate base, to be used in the extraction, as indicated in the parent application, it has been found that trialkyl amines having a total of at least 18 carbon atoms, and preferably from 24–42 carbon atoms, are most desired. Among the ones identified in the parent application, tridodecylamine presently appears preferred. However, in general it is believed that while tertiary amines are preferred, substituted tertiary amines and in some instances even primary or secondary amines may also be used, provided they are sufficiently water-immiscible and perform as weak or moderate bases. It is foreseen that, in many instances, primary amines may have sufficient water solubility to be undesirable with respect to possible contamination of the aqueous phase. It is also foreseen, that in some instances, primary or secondary amines may have too great a propensity to react with the lactic acid to form an amide, to be fully preferred. However, there is no theoretical reason why at least some secondary or primary amines could not be used, under certain circumstances.

Although the general principles have been described with respect to conduct of the extraction with either a weak base or a moderate base (or mixture of both), in general it is believed that if a weak base is used alone, the extraction results will not be as great as preferred because the weak base typically will prefer the undissociated acid, which was the weaker acid used for acidulation. The lactic acid, which is largely dissociated, is thus less effectively extracted by a weak base (when the weaker acid is used). Thus it is foreseen that if a weak base is to be used, it will generally be preferred to use it in a mixture with a moderate base as well. A weak base is typically used as a co-solvent (or solvent) in the watsolvent) in the water-immiscible phase, with a moderate base also present to facilitate extraction.

In the parent application, it was explained that while a variety of extraction processes may be used, it was foreseen that countercurrent extraction processes would be preferred. In addition to providing for countercurrent contacting of the two liquid phases, preferably the extraction unit used should provide for good removal and flow of the solids formed during precipitation of the salt of the moderate to weak acid. In the preferred processes described, this would be the bicarbonate salt of the cation in the fermentation broth. Typically the cation will be $Na^+$. In the most preferred embodiments, wherein the lactate feed treated and extracted has a greater than 3 mol. lactate concentration and the extraction is conducted with a water-immiscible trialkyl amine, the aqueous phase is relatively small in volume and, may for a slurry with the solid precipitate.

In the parent applications, solvents and/or diluent for the trialkyl amines, i.e. solvents and/or diluents for the water-immiscible bases, were described. In general, the selection of solvent will be controlled by a variety of factors such as boiling point, water solubility, and ability to enhance the extraction efficiency of the water-immiscible moderate base. However, in general when the lactic acid recovery is from a lactate containing fermentation broth, it is desired that the extraction occur within as short a period of time of the generation of the fermentation broth as possible, for commercial efficiencies. Most fermentation broths are separated from the fermentation process at a temperature of about 50° C., in typical commercial operations. Thus, unless time is used in substantial cooling, or cooling equipment is used, the extraction will typically occur of an aqueous solution having a temperature of at last 35° C., usually about 40–50° C.

If a back-extraction is used to recover the lactic acid from the organic phase, preferably the aqueous phase used during the back-extraction is at a higher temperature than the aqueous phase from which the lactic acid is separated in the first instance. This helps increase recovery efficiencies. Preferably the temperature of the back-extraction is as high as reasonably possible. Indeed, preferably it is conducted at a temperature of at least 100° C., and typically and preferably at least 135° C.

When a solvent and/or diluent is present in the organic phase, as will generally be preferred, the extraction is preferably conducted below the boiling point of the solvent and/or diluent. Thus, the temperature of the desired aqueous phase will, in some instances, dictate the preferred solvent used. It has been found that a mixture of paraffin (Isopar K, from Exxon) and octanol is a desirable solvent for the organic phase, and the use of octanol allows extraction temperatures up to about 140°–160° C. The mixture would preferably comprise about 50% trialkyl amine, 30% n-octanol and 20% non-aromatic paraffin, by weight.

It is noted that in some instances the solvent (or co-solvent) in the water-immiscible phase will function as a weak base and thus be capable of some modest amount of extraction. This would be true, for example, when the solvent is an alcohol or a ketone. However, alcohols and ketones are generally such weak bases that their operation in extracting the lactic acid is more akin to a salvation process than a more tightly associated ion attraction with the lactic acid. Thus the presence of at least some moderate base, such as the amine bases, is generally preferred. The presence of a polar solvent such as an alcohol or ketone can enhance the ability of a moderate base, such as a water-immiscible amine, to extract an acid, such as lactic acid.

If the organic phase is back-extracted, for final recovery of the lactic acid, in some instances it may be preferable to conduct the back-extraction under carbon dioxide pressure, in order to facilitate the extraction. For example, if the primary extraction was conducted under carbon dioxide pressure, the conduct of the back-extraction under pressure will prevent $CO_2$ release or the need to repressurize the escaping $CO_2$.

In preferred applications, the step of acidifying includes acidifying the aqueous phase from a fermentation process, to form sodium bicarbonate in the aqueous phase; and, the process includes using the sodium bicarbonate to form sodium lactate in the first aqueous phase, in later processing. This latter step may include forming sodium carbonate from the sodium bicarbonate and then putting the sodium carbonate in a fermentation process.

DESCRIPTION OF THE DRAWING

The single FIGURE of the drawing is a block diagram representing the preferred embodiment of the process according to the present invention.

DESCRIPTION OF A PREFERRED EMBODIMENT OF THE PROCESS

With reference to the drawing, lactic acid fermentation is carried out in a fermentor 10 in which carbohydrates are fermented and converted to lactic acid by the bacterial genus Lactobacillus and more specifically by the microorganism *Lactobacillus acidophilus*. Because many organisms which are attractive in such a fermentation process cannot tolerate acidic conditions with a pH lower than about 3.8, the acids formed by this process must be at least partly neutralized to maintain the pH above such level and more preferably above a pH of 4.5 to allow the fermentation to continue. In accordance with the preferred process, a neutralizing agent such as the alkali metal, alkaline earth metal or ammonium hydroxides, carbonates or bicarbonates are used for this purpose. In the preferred process, sodium carbonate ($Na_2CO_3$) is added to the fermentor 10 for this purpose, either via the recycle 12 as discussed below or along the path 13. Preferably, sufficient sodium carbonate or other alkaline substance is provided to the fermentor 10 to maintain the pH of the fermentation broth at a pH above 5.0 and preferably in the range of about 5.0 to 7.0, more preferably in the range of about 5.5 to 6.5 and most preferably in the range of about 6.0 to 6.5. Other ingredients may also be used in the fermentation process which is well known in the art.

In the fermentor 10, the carbohydrate is converted to lactic acid which immediately is converted to a lactate form in the presence of the neutralizing agent. In the preferred process using sodium carbonate, sodium lactate [$NaCH_3CH(OH)COO$] is formed. A portion of the fermentation broth or liquor is continuously or intermittently withdrawn from the fermentor 10 via the path and exposed to a filtration and concentration unit 15. The unit 15 functions to physically remove, via filtration or ultrafiltration, biomass and other solids which can be recycled to the fermentor 10, if desired. The filtrate comprises an aqueous lactate solution which contains the lactate salt comprised of the lactate anion together with the cation of the neutralizing agent. In the preferred process, the filtrate is comprised principally of sodium lactate. This solution, which commonly comprises between about 0.25% and 50% by weight of sodium lactate, may be concentrated by water evaporation or other techniques to improve the overall lactic acid production efficiency. In the preferred process, the filtered lactate solution is concentrated by water evaporation to about 40% to 70% by weight sodium lactate; however, such concentration is optional.

The sodium lactate solution exiting from the filtration and concentration unit 15 comprises a lactate feed solution which is fed into an extraction unit 18 along the path 16. The unit 18 is part of an extraction system which also includes the extractant regeneration unit 22, the organic phase stream 21 and the extractant recycle stream 24. Within the unit 18, the lactate feed solution is combined with an extractant comprised of at least one water-immiscible trialkyl amine in the presence of carbon dioxide, where the amine has a total of at least 18 carbon atoms. Within the unit 18, two separate phases are formed: an organic phase containing the extractant and extracted lactic acid and an aqueous or aqueous-slurry phase containing the carbonate or bicarbonate salt of the cation of the neutralizing agent. In the preferred process, the aqueous phase contains sodium carbonate or bicarbonate. The unit 18 may comprise any one of a variety of single or multi-stage pressure extraction units. In the preferred process, the unit 18 is a multi-stage countercurrent extraction unit.

In the preferred process, the extraction system is initially charged with the trialkyl amine. The amine may be introduced by directly adding it to the unit 18 or by adding it to the recycle stream 24 through the amine make-up stream 17.

During steady state operation, little if any additional trialkyl amine will be needed. To the extent it is, however, it can be added to the recycle stream 24 via the make-up stream 17.

Carbon dioxide may be added directly to the unit 18 under pressure via the page 19a, to the organic recycle stream 24 under pressure via the path 19c, or to the aqueous lactate stream 16 under pressure via the path 19b. In the preferred process as illustrated, the organic recycle stream 24 is preloaded with carbon dioxide by adding carbon dioxide under pressure via the stream 19c prior to the unit 18. In any case, the carbon dioxide within the unit 18 should preferably be maintained at a partial pressure of at least about 50 psig, more preferably at a partial pressure of at least 75 psig and most preferably between about 150–500 psig.

Although it is believed that some extraction of lactic acid from a lactate solution is possible with any water-immiscible trialkyl amine in the presence of carbon dioxide, the particular degree of extraction will vary with the amine utilized and the carbon dioxide pressure. The degree of extraction can also be enhanced or otherwise affected by various solvents as described below and as known in the art. The degree of extraction will generally be dependent on the partition coefficient and the number of stages used in the extraction process. As used herein, the partition coefficient is the mass concentration of lactic anion in the organic phase divided by the mass concentration of lactate expressed as lactic acid equivalent in the aqueous phase. Usually, for a particular system, the partition coefficient, within limits, will vary directly with the carbon dioxide pressure. As the partition coefficient increases, the number of stages needed to achieve a particular degree of extraction will decrease. Carbon dioxide and amine composition should preferably be sufficiently high to avoid excessive extractant phase necessary to extract the acid.

The trialkyl amines which are useful in the process of the present invention are those which are water-immiscible and relatively weak. Specifically, these are the trialkyl amines having a total of at least 18 carbon atoms and preferably about 24 to 42 carbon atoms. The practical lower limit of the number of carbon atoms is limited by the increasing water solubility of the smaller trialkyl amines or their salts. The water immiscibility of the trialkyl amines with 18 or more carbon atoms is well known in the art. The practical upper limit of the number of amine carbon atoms is determined by the molar concentration of amine obtainable in the organic phase. Specifically, the extraction ability of the trialkyl amines is dependent on the molar concentration of the amine component. Thus, as the molecular weight of the amine increases, the molar concentration of the amine component (or a pure amine solution) will decrease. The trialkyl amine should also be sufficiently strong to extract the lactic acid from the aqueous lactate feed, but sufficiently weak to enable water to back extract the lactic acid from the organic phase. Typical examples of such amines which meet the above requirements, are readily available and are useful in the process of the present invention are one or more of trihexylamine, trihexylamine, trioctylamine, triisooctylamine, tricaprylylamine, tridodecylamine and mixtures thereof.

The particular ratios of lactate feed solution and trialkyl amine phase which are fed to the unit 18 along the paths 16 and 24, respectively, will depend on a variety of factors including the concentration of the sodium lactate and the concentration of the amine. Preferably, the introduction of these materials should be such as to result in a substantially complete extraction of lactic acid from the lactate solution with the number of stages utilized. More preferably, the feed ration of amine phase to lactate solution should be about 40:1 to 1:2 and most preferably about 15:1 to 1:1 by weight.

The trialkyl amine provided to the unit 18 may be introduced in a substantially pure or a diluted form. Because many of the amines applicable to the present process and their salts are relatively viscous, it is preferably to introduce such amines with a solvent. In general, any composition which is miscible with the subject amines and their salts within the range of compositions used and which is reactively inert relative to the system components may be used in the present process. These solvents may be used to control viscosity, enhance extraction or stabilize the organic phase in a manner generally known in the art. Typical examples of solvents which can be used in the present process include liquid hydrocarbons such as kerosene or mineral oil, alkanols such as isopropanol, n-butanol and n-octanol and various ketones such as methyl-isobutyl ketone (MiBK) and nonanone, among others. The extractant used in the process of the present invention may comprise 100% of the trialkyl amine. A more preferred extractant, however, comprises up to about 70% by weight of a solvent or should comprise about 30%–95% by weight of the amine and about 5%–70% by weight of the solvent.

Following extraction within the unit 18, a lactic acid-rich organic phase comprised of lactic acid and the extractant is withdrawn along the path 21 and an aqueous phase or slurry comprises principally of carbonate and/or bicarbonate is withdrawn along the path 20. As used in the description of the preferred embodiment, the term carbonate or bicarbonate refers to the carbonate or bicarbonate salt of the cation of the substance used to neutralize the fermentation. Within the aqueous phase or slurry of the preferred embodiment, the predominant carbonate or bicarbonate is sodium bicarbonate which exists principally as sodium bicarbonate crystals. These are separated from the aqueous raffinate in the solid-liquid separation unit 25. The unit 25 can comprise various filtration, centrifugation or other solid-liquid separation means known in the art. Preferably, however, the sodium bicarbonate crystals are separated by filtration. The aqueous filtrate which in the preferred process is substantially free of lactate may be removed as a component of animal feed or as waste along the path 26. It is also possible, if desired, to recycle all or part of the filtrate back into the system through the streams 11, 14 or 16.

The separated sodium bicarbonate is then directed along the path 29 to a conversion and purification unit 30 for conversion of the sodium bicarbonate to sodium carbonate. Means are known in the art for accomplishing this conversion. In the preferred process, however, the sodium bicarbonate crystals are decomposed in boiling water to produce carbon dioxide and dissolved sodium carbonate. The solution of sodium carbonate is then purified by active carbon treatment and recycled along the path 12 as an alkaline or neutralization component in the fermentation process. The released carbon dioxide can also be reused, if desired. Since the preferred process utilizes sodium carbonate as the neutralizing component in the fermentation process, the aqueous phase after fermentation (stream 14) is comprised of sodium lactate. It is contemplated that other alkali metals, alkaline earth metals or ammonium hydroxides, carbonates or bicarbonates may also be used as the neutralizing agent, in which event the cations in the aqueous phase would be altered accordingly.

The lactic acid-rich organic phase is withdrawn from the unit 18 along the path 21. In the preferred process, the organic phase is decompressed in the flash unit 32 as it leaves the unit 18. This results in the release of a majority of the dissolved carbon dioxide via the stream 33 which may be recycled to streams 19a, 19b or 19c, if desired. This organic phase is made up principally of lactic acid and the extractant. Lactic acid is separated or recovered from this phase in the extraction unit 22, leaving a lactic acid-lean or depleted organic phase which is preferably recycled back to the extraction unit 18 along the path 24 in the form of regenerated extractant. As described above, carbon dioxide may also added to the recycle stream 24 via the path 19c to load the amine prior to the unit 18. The lactic acid solution is removed from the unit 22 as product via the stream 28.

In the preferred process, the unit 22 is a liquid/liquid extraction unit within which the lactic acid-rich organic phase is back extracted with water introduced along the path 23. Because of the relatively weak amine being used in the primary extraction process and because the amine is water-immiscible, the water is able to extract the lactic acid from the amine to form an aqueous solution of lactic acid of acceptable concentration.

In the case where the trialkyl amine is diluted with an appropriate solvent, such solvent becomes a part of the organic phase withdrawn from the unit 18 along the pat 21. Some solvents, such as alkanols and ketones, modify and enhance the lactic acid uptake into the organic phase. It is preferable to remove such solvents prior to the back extraction with water in the unit 22. This separation of the solvent from the lactic acid-rich organic phase can be accomplished by various separation techniques known in the art. Preferably, when possible, the separation is by azeotropic steam distillation within the unit 27. The removed solvent from the separation unit 27 may then be recycled along the pat 31 for regeneration of the extractant and use in the primary extraction, if desire.

The lactic acid can also be separated or recovered from the organic phase by vaporization or distillation of the lactic acid. Removal by distillation should preferably be performed at reduced pressure and elevated temperature conditions. Most preferably, the separation should be accomplished at pressures of from about 0.2 to 100 mm Hg and at temperatures from about 80° C. to about 240° C. If this distillation option is employed, the trialkyl amine should have a total of at least 24 carbon atoms, or be sufficiently nonvolatile to allow lactic acid fractionation from the amine by vacuum distillation.

The vaporization conditions will also remove alkanols or ketones, if present, as well as other solvent components more volatile than the trialkyl amine. These can be separately recovered and may be returned to the depleted extractant before it is cycled back to the extraction step. The vapor of lactic acid thus formed may also be directly fed, if desired, to an esterification process for reaction and further purification.

With the above process, lactic acid can be separated and/or removed from a lactate fermentation broth. Under optimal conditions, such separation and/or recovery can approach total recovery of the lactic acid, greater than 95% of that produced by fermentation. Of equal or greater importance is the ability of this recovery to be accomplished with the generation of minimal, if any, waste salt and under circumstances where substantially all of the extraction, conversion and other components used in the process can be recycled for reuse within the process. Still further, the process is significantly less energy intensive than competing processes and results in minimal, if any, plant emissions.

The preferred process has been described with respect to producing lactic acid from a lactate solution formed via a fermentation process. The present process is, however, application to the separation and/or recovery of lactic acid from a lactate solution regardless of its origin. For example, polylactide is a biodegradable polymer produced from lactic acid. Polylactide can be recycled by hydrolysis of the polymer to yield a lactate salt. The present process can then be used to recover lactic acid from the lactate salt for reuse in formation of the polylactide polymer.

Further details of the present process are shown and described in the following specific examples.

EXAMPLE 1

A lactate fermentation broth containing 10% by weight of NaCH$_3$CH(OH)COO (sodium lactate) was withdrawn from a fermentor in which pure carbohydrates were fermented by *Lactobacillus delbrueckii* in the presence of sodium carbonate in order to maintain a pH of 5.5, all as known in the art. The biomass and other solids were removed from the fermentation broth by filtration through ultrafiltration membranes and then concentrated by water evaporation to 50% by weight sodium lactate.

150 g/min of this sodium lactate solution were fed to a 5-state mixer-settler battery counter-currently to 1050 g/min of regenerated extractant comprising 48% by weight tricaprylylamine (Alamine 336™ produced by Henkel), 20% by weight n-butanol and 32% by weight aromatic-free kerosene. The extraction system was kept at ambient temperature and a 240 psig CO$_2$ atmosphere was maintained therein. Sodium bicarbonate crystals formed in the aqueous phase as of the second mixer-settler.

The aqueous phase was withdrawn and sodium bicarbonate was filtered off from the aqueous raffinate which was practically free of lactate values. The sodium bicarbonate crystals were decomposed in boiling water to CO$_2$ and to dissolved sodium carbonate. This solution was purified by active carbon treatment to a form suitable for use as a base in the fermentation.

The organic phase withdrawn from the last stage of the mixer-settler battery contained 0.65 mole lactic acid per kg. CO$_2$ was allowed to escape from the organic phase, following which the butanol was separated and removed by azeotropic steam distillation. The remaining organic phase was back-extracted with hot water to form a lactic acid-depleted organic phase and an aqueous solution of the lactic acid. The separated butanol was reintroduced into the back-extracted organic phase to regenerate the extractant while the aqueous phase was concentrated and fed to final purification. Removal of lactic acid from the lactate feed solution was about 95%.

EXAMPLE 2

Aqueous solutions of sodium lactate were equilibrated in a pressure vessel with various extractants under a 220 psig CO$_2$ atmosphere. Contact temperature was 20° C. The initial pH of the aqueous phase and equilibrium data are summarized in the Table below.

TABLE 1

| | | Equilibrium data | |
|---|---|---|---|
| Extractant composition | Initial aqueous pH | sodium lactate aqueous (wt %) | lactic acid organic (wt %) |
| n-butanol | 5.5 | 6.2 | 1.05 |
| 80% TDA + 20% i-PrOH | 5.5 | 29.2 | 10.6 |
| 80% TDA + 20% hexane | 5.5 | 39.8 | 2.9 |
| 67% TCA + 33% n-OctOH | 10.9 | 50.3 | 14.3 |
| 70% TCA + 30% n-BuOH | 10.9 | 50.3 | 15.0 |
| 48% TCA + 20% n-BuOH + 32% kerosene | 10.7 | 46.9 | 9.3 |

TDA = tridodecylamine (Henkel)
TCA = tricaprylylamine
i-ProOH = isopropanol
n-OctOH = n-octanol
n-BuOH = n-butanol

EXAMPLE 3

An extractant mixture comprised of 80% by weight tridodecylamine (Alamine 304-1) produced by Henkel) and 20% by weight n-butanol, was contacted with 30% by weight aqueous lactic acid (Purac) in sufficient quantity to produce a loading of 6.9% by weight lactic acid in the organic phase. 230 g of this material was added to a stirred round bottom flask connected to a distillation apparatus, condenser, and controlled vacuum system. The solution was heated to 219° C. at a pressure of 2 mm Hg. Initial condensate fractions included butanol and water. A later fraction showed recovery of 97% by weight of the original lactic acid. The residual extractant contained 0.2% by weight lactic acid. The composition of the pooled fractions containing the acid was 98.3% by weight aqueous lactic acid and 1.7% by weight of its oligomers. The depleted extractant was replenished with butanol and cycled back for another extraction. Five such cycles were rn on one batch without significant loss of extractant performance.

EXAMPLE 4

Various experiments were conducted in a Parr pressure reactor for the purpose of showing the applicability of the process of the present invention to a broad range of $CO_2$ pressures, to a variety of solvents and to representative samples of trialkyl water-immiscible amines with a total carbon content of at least 18.

The apparatus comprised a Parr pressure reactor with four agitators, gas inlet and outlet ports, aqueous and organic sample ports and a pressure gage. The procedure involved adding the aqueous and the pre-mixed organic solutions to the Parr reactor. Except for Experiment Nos. 7, 12, 18 and 21 below in which the ratio of organic to aqueous was 1:3, the ratio of organic to aqueous in all experiments was 1:1. The aqueous solution was comprised of sodium lactate (NaLa), calcium lactate (CaLa) or potassium lactate (KLa). The NaLa solutions comprised about 20%–40% by weight of the lactate, the KLa solution comprised about 20% by weight of the lactate, while the CaLa solution comprised about 6% by weight of the lactate. Further, in Experiment Nos. 7–10, 12–18 and 20–24, 10% by weight sodium bicarbonate was added for the purpose of saturating the solution. The organic solution comprised a trialkyl amine or a mixture of a trialkyl amine and one or more solvents.

The Parr pressure reactor was then assembled and a slow flow of $CO_2$ was introduced for about 5 minutes to purge the air in the reactor. The $CO_2$ pressure was then adjusted to the desired level. It should be noted that the pressures identified in the table below are gage pressures. Thus, a $CO_2$ level of 0 psig as indicated in Experiment Nos. 1 and 13 reflect a $CO_2$ partial pressure of 14.7 psi. The $CO_2$ pressure was maintained at the selected level, with a slow bleed of $CO_2$ (about 100 ml/min) bubbling through the contents, and the contents in the reactor were agitated for two hours. The $CO_2$ inlet and outlet ports were then sealed and agitation continued for 10 more minutes, at which time agitation was terminated and the contents were allowed to settle for 30 minutes. Samples of both the organic and aqueous phases were collected through the organic and aqueous sample ports, after which the above procedure repeated for a different $CO_2$ pressure. All experiments were run at 25° C.

All organic samples were analyzed with NaOH to a phenolphthalein endpoint to determine concentration of lactic acid in the organic phase. All aqueous samples were analyzed by HPLC to determine lactic acid equivalent in the aqueous phase. The partition coefficient (K) was then calculated by dividing the concentration of lactic acid in the organic phase by the concentration of lactate, expressed by lactic acid equivalent, in the aqueous phase.

The table below reflects data from selected experiments conducted in accordance with the above procedure in which the amines and solvents are identified as follows. All percentages are by weight unless otherwise specified.

| Amines | Solvents |
| --- | --- |
| A1 = trihexylamine | CS1 = n-octanol |
| A2 = trioctylamine | CS2 = n-butanol |
| A3 = triisooctylamine | CS3 = nonanone |
| A4 = tricaprylylamine | CS4 = Isopar K, Exxon |
| A5 = tridodecylamine | |

TABLE 2

| No | Organic | Aqueous | $CO_2$ Press. (psig) | K C (org)/C (aq) | Final Aq. Wt % Lac. |
| --- | --- | --- | --- | --- | --- |
| 1 | A4 (48%), CS1 (30%), CS4 (22%) | CaLa | 0 | 0.068 | 2.21 |
| 2 | A4 (48%), CS1 (30%), CS4 (22%) | CaLa | 150 | 0.388 | 2.06 |
| 3 | A4 (48%), CS1 (30%), CS4 (22%) | CaLa | 220 | 0.553 | 1.99 |
| 4 | A4 (48%), CS1 (30%), CS4 (22%) | CaLa | 300 | 0.622 | 1.93 |
| 5 | A4 (48%), CS1 (30%), CS4 (22%) | KLa | 75 | 0.112 | 18.5 |
| 6 | A4 (48%), CS1 (30%), CS4 (22%) | KLa | 500 | 0.198 | 17.5 |
| 7 | A4 (48%), CS1 (30%), CS4 (22%) | NaLa (sat) | 75 | 0.047 | 19.9 |
| 8 | A4 (48%), CS1 (40%), CS4 (12%) | NaLa (sat) | 150 | 0.093 | 38.3 |
| 9 | A4 (48%), CS1 (40%), CS4 (12%) | NaLa (sat) | 200 | 0.155 | 38.0 |
| 10 | A4 (48%), CS1 (40%), CS4 (12%) | NaLa (sat) | 300 | 0.199 | 37.5 |
| 11 | A4 (48%), CS2 (35%), CS4 (17%) | NaLa | 220 | 0.255 | 29.8 |
| 12 | A1 (33%), CS1 (30%), CS4 (37%) | NaLa (sat) | 240 | 0.123 | 20.1 |
| 13 | A2 (43%), CS1 (30%), CS4 (27%) | NaLa (sat) | 0 | 0.038 | 21.9 |
| 14 | A2 (43%), CS1 (30%), CS4 (27%) | NaLa (sat) | 75 | 0.064 | 21.6 |
| 15 | A2 (43%), CS1 (30%), CS4 (27%) | NaLa (sat) | 240 | 0.119 | 20.7 |
| 16 | A4 (48%), CS3 (52%) | NaLa (sat) | 240 | 0.069 | 21.6 |
| 17 | A3 (43%), CS1 (30%), CS4 (27%) | NaLa (sat) | 75 | 0.038 | 20.3 |
| 18 | A3 (43%), CS1 (30%), CS4 (27%) | NaLa (sat) | 240 | 0.097 | 20.0 |
| 19 | A5 (48%), CS2 (20%), CS4 (32%) | NaLa | 220 | 0.266 | 34.4 |
| 20 | A4 (100%) | NaLa (sat) | 75 | 0.020 | 21.4 |
| 21 | A4 (100%) | NaLa (sat) | 240 | 0.047 | 21.4 |
| 22 | A4 (43%), CS1 (30%), CS4 (27%) | NaLa (sat) | 500 | 0.208 | 19.8 |
| 23 | A4 (48%), CS3 (52%) | NaLa (sat) | 500 | 0.102 | 21.3 |
| 24 | A4 (48%), CS4 (52%) | NaLa (sat) | 500 | 0.020 | 21.8 |

EXAMPLE 5

Extraction of Lactate Feeds at Various Conditions

Sodium and potassium lactate solutions were prepared stoichiometrically from lactic acid solutions. A304 is Alamine 304, Trilaurylamine from Henkel Corp. The concentration was adjusted to 1 mol/kg by diluting with Parasol, a non-aromatic kerosine solvent, boiling range 210–275° C., from Paz Company of Israel. The alcohols were supplied by Merck or Frutarom of Israel.

The pressure experiments were carried out in a Parr bench-top mini reactor (Serial 4560, 300 ml autoclave). $CO_2$ was supplied via a cylinder. The control panel regulated the heating and measured internal pressure in psi. Stirrer speed was 600 rpm. At each pressure level a stable pressure was held for 15–20 minutes to ensure complete equilibrium and then phase separation for a further 15–20 minutes. Samples were taken (for Table 3 experiments) from the organic phase, which were usually clear. Free $CO_2$ volume was measured by water displacement. Lactic acid concentration was determined by titration with 0.1 N NaOH and phenolphthalein indicator after warming the sample for removal of extracted $CO_2$.

| Materials | |
|---|---|
| A336 | Alamine 336, Tri-Caprylyl Amine ($C_8$–$C_{10}$). Henkel Corp. commercial product |
| DEHPA | Di-(2-ethylhexyl) Phosphate Sigma, Anhydrous reagent |
| i-AmOH | Merck A.R. |
| 1-BuOH | Frutarom A.R. |
| 2-BuOH | Frutarom A.R. |
| i BuOH | Merck A.R. |
| n-Octanol | Merck A.R. |
| Lactic acid (LaH) | Merck A.R., 90% solution |
| MIBK | Methylisobutylketone Frutarom C.P. |
| MTCA | Aliquat 336, Methyltricapryl amine chloride, Henkel Corp. |
| n-Butyl Acetate | BDH GPR |
| Parasol | Kerosine solvent <1% aromatics, boiling range 210–275° C., Paz Company |

TABLE 3

| Exp | Amine | Conc. | Modif. | Conc. | Aqueous | Initial Conc. | Pressure psi | Temp ° C. | Loading Org. Phase mol/kg | $CO_2$/gm Org. Phase cc | Phase Ratio org/aq | $H_2O$ Org. Phase % | Conversion/ Extraction % |
|---|---|---|---|---|---|---|---|---|---|---|---|---|---|
| 19 | A304 | 1 mol/kg | 2-BuOH | 20% | NaLa | 40% | 87 | 14° | 0.27 | | 3 | | |
| | | | | | | | 145 | | 0.43 | | | | |
| | | | | | | | 212 | | 0.539 | | | | |
| 20 | None | | 2-BuOH | 100% | NaLa | 40% | 85 | 14° | 0.114 | | 3 | | |
| | | | | | | | 146 | | 0.1 | | | | |
| | | | | | | | 218 | | 0.113 | | | | |
| 21 | A304 | 1 mol/kg | 2-BuOH | 20% | NaLa | 5% | 88 | 14° | 0.053 | | 3 | | |
| | | | | | | | 146 | | 0.069 | | | | |
| | | | | | | | 217 | | 0.082 | | | | |
| 22 | A304 | 1 mol/kg | 2-BuOH | 20% | KLa | 8.30% | 87 | 13° | 0.021 | 15.3 | 3 | | |
| | | | | | | | 147 | | 0.019 | 22.9 | | | |
| | | | | | | | 218 | | 0.027 | 36.7 | | | |
| 23 | A304 | 1 mol/kg | 2-BuOH | 20% | NaLa | 20% | 218 | 18° | 0.228 | | 3 | | |
| 24 | A304 | 1 mol/kg | 2-BuOH | 20% | NaLa | 10% | 218 | 14° | 0.1 | 35.9 | 3 | | |
| 25 | A304 | 1 mol/kg | i-BuOH | 30% | NaLa | 56% | 238 | 18° | 0.923 | 73.9 | 3 | | 57.4 |
| 26 | A304 | 1 mol/kg | i-BuOH | 30% | NaLa | 56% | 240 | 18° | 0.785 | 43.4 | 5 | 1.41 | 82.1 |
| 27 | A304 | 1 mol/kg | i-BuOH | 30% | KLa | 59% | 238 | 18° | 0.657 | 39.9 | 5 | 1.26 | 71.9 |
| 28 | A304 | 1 mol/kg | i-PrOH | 20% | NaLa | 56% | 244 | 0° | 0.831 | 90.0 | 5 | 1.46 | 86.1 |
| | | | | | | | 238 | 16° | 0.781 | 40.1 | 5 | 1.01 | 82.0 |
| | | | | | | | 237 | 50° | 0.464 | 62.5 | 5 | 1.44 | 47.7 |
| 29 | A304 | 1 mol/kg | EtOH | 15% | NaLa | 56% | 239 | 0° | 0.655 | 73.6 | 5 | 1.4 | |
| 30 | A304 | 1 mol/kg | i-PrOH | 20% | NaLa | 56% | 237 | 0° | 0.707 | 62.7 | 5 | | 67.7 |
| | | | | | | | 238 | 17° | 0.859 | 44.0 | 5 | | 83.3 |
| 31 | A304 | 1 mol/kg | EtOH | 15% | NaLa | 51.80% | 238 | 20° | 0.722 | 48.2 | 5 | | 75.5 |
| 32 | None | | EtOH | 100% | NaLa | 51.80% | 236 | 21° | 0.143 | 75.1 | 5 | | |
| 33 | A304 | 1 mol/kg | n-Octanol | 20% | NaLa | 51.80% | 240 | 20° | 0.526 | 34.1 | 7 | | 75.9 |
| 34 | A304 | 1 mol/kg | i-PrOH | 30% | NaLa | 51.80% | 241 | 18° | 0.848 | 43.4 | 5 | | |
| | | | | | | | 240 | 40° | 0.803 | 31.82 | 5 | | |
| | | | | | | | 238 | 59° | 0.593 | 31.36 | 5 | | |

EXAMPLE 6

Extraction With Variations in Extractant and pH

| Materials | |
|---|---|
| A304 | Alamine 304, Trilauryl Amine. Henkel Corp. commercial product |
| Primene JM-T | 5-Alkyl Primary Amine (a primary aliphatic amine with highly branched alkyl chains, nitrogen is bonded directly to a tertiary carbon, $R_1C(R_2) (R_3)NH_2$) ROHM & HAAS, commercial product |
| TBP | Tri-Butyl Phosphate Riedel-de Haen 99% solution |
| TOPO | Trioctylphosphine oxide, Sigma 90% tech |
| Xylene | Frutarom A.R. |

Methods

Distribution curves were determined by limiting condition experiments carried out in 100 ml erhlenmeyers. Analysis of clear organic phase for loading of lactic acid was by direct titration with NaOH 0.1N in isopropanol using phenolphthalein as indicator. The aqueous phases were similarly analyzed in $H_2O$.

Sodium lactate solutions at the various concentrations and pH's were prepared stoichiometrically from lactic acid solutions then adjusted to the required pH. The extraction curves for the various extractants and solvents were made at limiting conditions and analysis as above on clear organic phase.

For all experiments the lactic acid was diluted from the original bottled solution (90%) and hydrolysed by refluxing for 4–6 hours.

constructed to allow conveying settled solids along the bottom to the discharge pipe, which is also designed to avoid plugging by solids.

2. Raining bucket contactors, also known as Graesser extractors, constructed as a pressure vessel, with modified internals to allow the smooth conveyance of a viscous slurry in the aqueous phase.

3. Agitated or stirred column extractors, constructed as a pressure vessel and with modified internals to allow the smooth raining of the slurry. Pulsing of flow or agitation of the column internals is preferred to prevent buildup of solids in the process.

The extractor (18) should be operated such that at least about 90% of the incoming lactate values are converted to lactic acid and are extracted into the extractant in one pass.

TABLE 4

| Organic Phase | pH = 2–2.3 | pH = 3–3.1 | pH = 4–4.1 | ph = 4.9 | pH = 6–6.3 | pH = 6.9 | pH = 8 |
|---|---|---|---|---|---|---|---|
| 1 mol/kg A304 in Parasol +10% i-BuOH | 1.26 | 1.07 | 0.57 | 0.057 | | 0.011 | |
| 1 mol/kg A304 in Parasol + 30% i-BuOH | 1.48 | 1.48 | 1.07 | 0.29 | | 0.011 | |
| 1 mol/kg A304 in Parasol + 20% n-octanol | 1.15 | | 0.49 | | 0.031 | | 0.000 |
| 1 mol/kg JMT in Parasol + 20% n-octanol | 1.05 | 0.97 | 0.89 | | 0.087 | | 0.028 |
| 1 mol/kg JMT in n-octanol | 1.15 | | 0.82 | | 0.089 | | 0.048 |
| 1-butanol | 0.87 | | 0.25 | | 0.000 | | 0.000 |
| iso amyl alcohol | 0.60 | | 0.22 | | 0.000 | | 0.000 |
| TBP | 0.74 | | 0.28 | | 0.016 | | 0.000 |
| 1 mol/kg TOPO in xylene | 0.75 | 0.68 | 0.56 | 0.21 | | 0.043 | |
| n-butyl acetate | 0.10 | | 0.032 | | 0.000 | | 0.000 |
| A304:Oleic acid 0.5 mol/kg | 0.35 | | 0.100 | | 0.000 | | 0.000 |
| 336:DEHPA 0.5 mol/kg | 0.39 | 0.33 | 0.26 | 0.082 | | 0.000 | |
| MTCA:DEHPA 0.5 mol/kg | 0.35 | | 0.24 | | 0.036 | | 0.030 |
| MTCA 1 mol/kg + 20% octanol | 0.59 | | 0.31 | | 0.019 | | 0.000 |

A Proposed Commercial Process

In the application of the disclosed invention, and based on laboratory and pilot data, a commercial process is foreseen to have the following preferred configuration and conditions. The process will be described with reference to numerals used in the figure.

Lactate fermentation by Lactobacillus would be conducted with a substrate (11) of dextrose, salts, and nutrients, controlled at pH 5 to 7 by addition of recycled sodium carbonate (12) in standard anaerobic fermentators (10). $CO_2$ evolved during fermentation would be recovered for reuse in the extraction. After fermentation is complete, the fermentation liquor (14) would be filtered (15) to remove biomass, carbon treated, and evaporated (15) to 40–70 wt % NaLa. The cells are discarded after the process.

The concentrated broth (16) would be pumped into the extraction unit and contacted for liquid-liquid extraction at about 40° C. and 300 psi in countercurrent flow with the extractant. The regenerated extractant (24) would enter the opposite end of the extraction unit. The extractant to broth flows would be maintained at flow ratios of about 10 to 1. The extractant would be composed of about 50 wt % tricaprylyl amine, 30 wt % n-octanol, and 20 wt % nonaromatic paraffin with nominal boiling range of 180–200° C.

The extraction unit (18) can be any one of many industrially proven differential or discrete countercurrent extractors which inherently or through modification are able to handle the solid slurry of sodium bicarbonate that is formed during the extraction, and should be of a type constructed to operate under pressures up to 500 psig and be designed to give about five equivalent equilibrium states. Three such extractors are:

1. Discrete stage mixer settlers, each mixer and settler stage constructed as pressure vessels, and each settler Remaining in the depleted broth, or raffinate, will be lactic acid, sodium bicarbonate, unfermented sugars, and other broth impurities. Sodium bicarbonate will be produced in amounts stoichiometrically equivalent to the moles of lactate converted. The final slurry phase raffinate (20) will have up to 50 wt % solid sodium bicarbonate after extraction.

Raffinate exiting the extractor (20) will preferably be flashed to atmospheric pressure, with the liberated $Co_2$ being captured for reuse. The raffinate solids (29) would be removed by centrifugation or filtration (25), washed with water and would be used to neutralize fermentation. In this way, sodium values are recycled. The aqueous raffinate (26) containing approximately 5–10% of the sodium values, plus all other impurities and lactate values of the raffinate (20), would be used in animal feed formulations. Sodium losses in raffinate should be made up (13).

Loaded extract from the extractor (18), with lactic acid content of greater than about 0.5 mol lactic acid/kg, would be flashed (32) to remove $Co_2$ (33), and the resultant stream (21) would be back-extracted in about five stages of an extractor train (22) in countercurrent contact with water (23). This extractant regeneration is operated at about 140° C. and 100 psig, with water to extractant flow ratios of about 2:1. Extractant regeneration can be carried out in one of many industrially available extraction devices, including mixer settlers, columns, or centrifugal extractors. The equipment must be designed to handle the elevated temperatures and pressures.

The regenerated extractant (24) with a lactic acid content of less than about 0.1 mol lactic acid/kg, would be saturated with $CO_2$ at 300 psig (19c), and added back to the extractor.

The resultant lactic acid stream (28), with a concentration of 15–20 wt %, would be treated with activated carbon, cation exchange, and evaporation, to produce heat stable lactic acid.

Carbon dioxide collected from flashing of raffinate (20) and loaded extractant (33), as well as from fermentation (10) and sodium bicarbonate decomposition (30) (if used), would be collected, purified, and recompressed for reuse in extraction (19c).

By the above description, it can be seen that sodium recycles from fermentation to extraction and back to fermentation. Extractant is recycled from extraction to extractant regeneration. Carbon dioxide is recycled from fermentation, bicarbonate decomposition, and flashing to extractant saturation. These three recycle schemes can provide for efficient and cost effective production of lactic acid while reducing the environmental impact of the production process.

What is claimed is:

1. A process for the recovery of lactic acid; said process including the steps of:
   (a) forming a multi-phase system including at least a first aqueous phase and a second, water-immiscible, liquid phase;
      (i) said first aqueous phase having a pH of 4 to 14 and including lactate salt in solution;
      (ii) said second water-immiscible phase including an extractant capable of forming a water-immiscible lactate salt, with a lactate-containing component;
   (b) extracting said first aqueous phase with said second water-immiscible phase by extracting the lactate-containing component by forming a water-immiscible lactate salt with the extractant;
      (i) said step of extracting including a step of acidifying at least one of said first aqueous phase and said second water-immiscible phase, by addition of acid thereto, without providing said first aqueous phase with a pH below 4;
   (c) separating a resulting water-immiscible phase from a resulting aqueous phase after said step of extracting; and
   (d) generating lactic acid from the lactate salt of the extractant, wherein said step of generating lactic acid comprises at least one of:
      (i) back-extracting the water-immiscible phase, resulting from said step of separating, with water; and
      (ii) vaporizing at least a portion of the water-immiscible phase, resulting from said step of separating.

2. A process according to claim 1 wherein:
   (a) said step of forming a multi-phase system includes providing a first aqueous phase having a temperature of 35°–50° C., while said step of extracting is conducted.

3. A process according to claim 1 wherein:
   (a) said step of back-extracting includes back-extracting with water at a temperature of at least 100° C.

4. A process according to claim 1 wherein:
   (a) said step of extracting comprises extracting at least 90% of all lactate-containing component initially present in the first aqueous phase, into said water-immiscible phase.

5. A process according to claim 1 wherein:
   (a) said step of extracting comprises extracting with an extractant containing base selected from the group consisting of: moderate bases; and, mixtures of moderate bases and weak bases.

6. A process according to claim 1 wherein:
   (a) said step of extracting comprises extracting with an extractant containing an amine base.

7. A process according to claim 6 wherein:
   (a) said step of extracting with an extractant containing an amine base comprises extracting with an extractant containing a tertiary amine.

8. A process according to claim 2 wherein:
   (a) said step of acidifying comprises acidifying with a weak acid.

9. A process according to claim 8 wherein:
   (a) said step of acidifying comprises acidifying with $CO_2$.

10. A process according to claim 9 wherein:
    (a) said step of acidifying comprises adding $CO_2$ to said second water-immiscible phase prior to said step of forming a multi-phase system.

11. A process according to claim 9 wherein:
    (a) said step of acidifying comprises adding $CO_2$ to said first aqueous, prior to said step of forming a multi-phase system.

12. A process according to claim 9 wherein:
    (a) said step of acidifying with $CO_2$ comprises adding at least one molar equivalent of $CO_2$ for each mole of lactate salt initially in the solution.

13. A process according to claim 9 wherein:
    (a) said step of acidifying with $CO_2$ comprises providing a partial pressure of $CO_2$, in the multi-phase system, of at least 50 psig.

14. A process according to claim 9 wherein:
    (a) said step of acidifying with $CO_2$ comprises providing a partial pressure of $CO_2$, in the multi-phase system, of at least 300 psig.

15. A process according to claim 1 wherein:
    (a) said step of acidifying comprises acidifying with a weak acid;
    (b) said step of extracting comprises extracting with an extractant that contains base selected from the group consisting of: moderate bases; and, mixtures of weak bases and moderate bases; and,
    (c) said first aqueous phase is derived from a lactate fermentation broth.

16. A process according to claim 15 wherein:
    (a) said first aqueous phase includes sodium lactate;
    (b) said step of acidifying with a weak acid comprises acidifying with $CO_2$; and,
    (c) said step of extracting comprises extracting with a trialkyl amine.

17. A process according to claim 16 wherein:
    (a) said step of acidifying includes forming sodium bicarbonate; and,
    (b) said process includes a step of recovering the sodium bicarbonate, and using it to generate sodium lactate in the first aqueous phase, in further processing.

18. A process according to claim 17 wherein:
    (a) said step of using sodium bicarbonate to generate sodium lactate comprises a step of forming sodium carbonate from the sodium bicarbonate.

19. A process for recovery of lactic acid; said process including the steps of:
    (a) forming a multi-phase system including a first aqueous phase and a second water-immiscible phase;
       (i) said first aqueous phase including lactate salt in solution;
       (ii) said second water-immiscible phase including lactic acid extractant;
    (b) extracting said first aqueous phase with said water-immiscible phase;
       (i) said step of extracting including a step of acidifying at least one of said first aqueous phase by addition of an acid thereto, and said water-immiscible phase under conditions wherein, at any given point, at least 50% of lactate-containing component in the aqueous phase remains in the lactate salt form; and (ii) said step of extracting comprises removing at least 90% of lactate-containing component, as lactic acid, from said first aqueous phase and into said water-immiscible phase;

(c) separating a resulting water-immiscible phase from a resulting aqueous phase after said step of extracting; and (d) generating lactic acid from the lactate salt of the extractant, wherein said step of generating lactic acid comprises at least one of:

(i) back-extracting the water-immiscible phase, resulting from said step of separating, with water; and (ii) vaporizing at least a portion of the water-immiscible phase, resulting from said step of separating.

20. A process according to claim 19 wherein:

(a) said step of forming a multi-phase system includes providing a first aqueous phase having a temperature of 35°–50° C., while said step of extracting is conducted.

21. A process according to claim 1, wherein:

(a) said step of vaporizing includes distilling at a pressure of from about 0.2 to 100 mmHg and at a temperature from about 80° C. to about 240° C.

22. A process according to claim 19, wherein:

(a) said step of back-extracting includes back-extracting with water at a temperature of at least 100° C.

23. A process according to claim 19, wherein:

(a) said step of vaporizing includes distilling at a pressure of from about 0.2 to 100 mmHg and at a temperature from about 80° C. to about 240° C.

* * * * *

UNITED STATES PATENT AND TRADEMARK OFFICE
CERTIFICATE OF CORRECTION

PATENT NO.   : 6,187,951 B1
DATED        : February 13, 2001
INVENTOR(S)  : Baniel et al.

It is certified that error appears in the above-identified patent and that said Letters Patent is hereby corrected as shown below:

Title page,
Item [75], Inventors: insert -- Jeffrey J. Kolstad, Wayzata, MN -- and -- Brenda F. Stewart, White Bear Lake, MN --
Item [56], References Cited, U.S. PATENT DOCUMENTS: insert the following references in the appropriate order:

| | | | |
|---|---|---|---|
| -- | 2,261,926 | 11/04/1941 | Nolte et al. |
| | 2,415,558 | 02/11/1947 | Hesler et al. |
| | 4,771,001 | 09/13/1988 | Bailey et al. |
| | 5,068,419 | 11/26/1991 | Kulprathipanja et al. |
| | 5,210,296 | 05/11/1993 | Cockrem et al. |
| | 5,641,406 | 06/24/1997 | Sarhaddar et al. |
| | 5,766,439 | 06/16/1998 | Eyal et al. |
| | 5,746,920 | 05/05/1998 | Boergardts et al. |
| | 5,773,653 | 06/30/1998 | Baniel |
| | 5,780,276 | 07/14/1998 | Baniel |
| | 5,786,185 | 07/28/1998 | Tsao et al. |
| | 5,831,122 | 11/03/1998 | Eyal -- |

FOREIGN PATENT DOCUMENTS, insert the following reference:

| | | | |
|---|---|---|---|
| -- | 1 049 846 | 02/05/1959 | (DE) |
| | 32 22 837 A1 | 12/22/1983 | (DE) |
| | 907,321 | 10/03/1962 | (GB) -- |

OTHER PUBLICATIONS, insert the following reference:
-- Tamada, J. et al., "Extraction of Carboxylic Acids with Amine Extractants. 1. Equilibria and Laws of Mass Action Modeling", *Ind. Eng. Chem. Res.*, Vol. 29, No. 7, pp. 1319-1326 (1990) --

Column 8,
Line 67, "for a slurry" should read -- from a slurry --

Column 11,
Line 53, delete the second occurrence of "trihexylamine"

UNITED STATES PATENT AND TRADEMARK OFFICE
CERTIFICATE OF CORRECTION

PATENT NO. : 6,187,951 B1
DATED : February 13, 2001
INVENTOR(S) : Baniel et al.

It is certified that error appears in the above-identified patent and that said Letters Patent is hereby corrected as shown below:

Column 13,
Line 15, "pat 21" should read -- path 21 --

Column 22,
Line 13, "aqueous, prior" should read -- aqueous phase, prior --

Signed and Sealed this

Thirtieth Day of March, 2004

JON W. DUDAS
*Acting Director of the United States Patent and Trademark Office*